United States Patent [19]

Christensen et al.

[11] 4,374,849
[45] Feb. 22, 1983

[54] 6-AMIDOCYCLONOCARDICINS

[75] Inventors: Burton G. Christensen, Cliffside Park; James V. Heck, Fanwood, both of N.J.

[73] Assignee: Merck & Co., Inc., Rahway, N.J.

[21] Appl. No.: 301,668

[22] Filed: Sep. 14, 1981

[51] Int. Cl.³ .................... A61K 31/40; C07D 487/14
[52] U.S. Cl. ............................. 424/274; 260/245.2 R
[58] Field of Search ................. 260/245.2 R; 424/274

[56]  References Cited

PUBLICATIONS

Aoki et al., The Journal of Antibiotics, May 1976, pp. 492–500.

*Primary Examiner*—Richard Raymond
*Attorney, Agent, or Firm*—James A. Arno; Hesna J. Pfeiffer

[57] ABSTRACT

Disclosed are 6-amidocyclonocardicins (I) and their pharmaceutically acceptable salts and esters which are useful as antibiotics

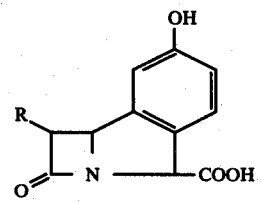

wherein: R is $NH_2$, $R^1$ NH, $R^1$ is acyl.

Also disclosed are processes for the preparation of such compounds; pharmaceutical compositions comprising such compounds; and methods of treatment comprising administering such compounds and compositions when an antibiotic effect is indicated.

4 Claims, No Drawings

6-AMIDOCYCLONOCARDICINS

BACKGROUND OF THE INVENTION

This invention relates to 6-amidocyclonocardicins (I) and the pharmaceutically acceptable salt and ester derivatives thereof which are useful as antibiotics:

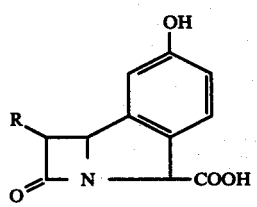

wherein: R is $R^1NH$; wherein $R^1$ is hydrogen or an acyl radical known to be effective in the related bicyclic β-lactam antibiotic art, such as, the penicillins, cephalosporins, and 6-amido penems and carbapenems. To the extent that the following U.S. patents define $R^1$ as acyl, they are hereby incorporated herein by reference: U.S. Pat. No. 4,217,453 (issued Aug. 12, 1980); U.S. Pat. No. 4,226,866 (issued Oct. 7, 1980).

This invention also relates to the carboxyl derivatives of I which are antibiotics and which may be represented by the following generic structure (I):

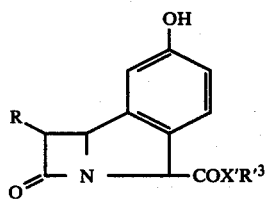

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens which representatively include both Gram positive bacteria such as *S. aureus, Strep. pyogenes,* and *B. subtilis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently be summarized by the following reaction diagram:

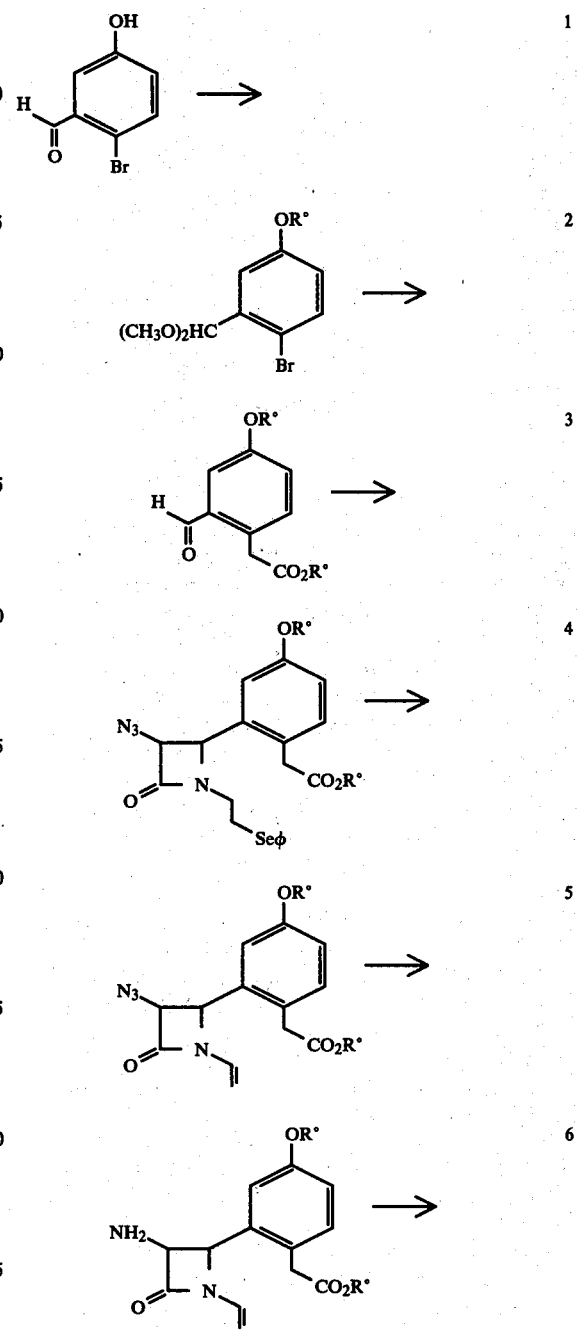

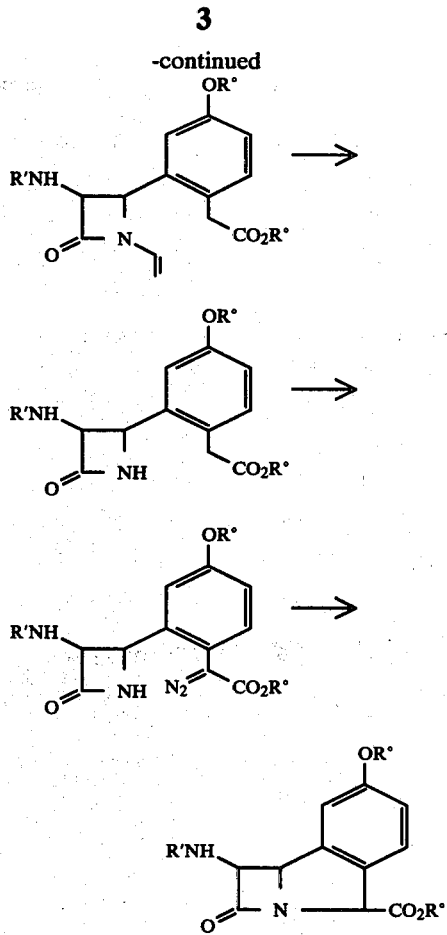

In words relative to the above reaction diagram, the transformation 1 to 2 is accomplished by treating 2-bromo-5-hydroxybenzaldehyde (1) with benzylbromide in the presence of base such as triethylamine, N,N-diisopropylethylamine, potassium carbonate or the like, in a solvent such as DMF, acetonitrile at 80° for 4 to 6 hours, followed by trimethylorthoformate and tosic acid in methanol at room temperature for 24 hours.

Metal-halogen exchange in the presence of a base such as n-butyllithium, t-butyllithium or the like in a solvent such as THF, diethylether, 1,2-dimethoxyethane or the like at a temperature of from −78° to −60° C. followed by transmetallation with one equivalent of CuBr-SMe₂ at −60° (1 hour), coupling with benzyl bromoacetate at a temperature of from −60° to −20° C. for 3 hours, followed by acid-catalyzed hydrolysis of the acetal function effects the conversion 2 to 3.

Condensation of aldehyde (3) with 2-(phenylselenenyl)ethylamine in the presence of magnesium sulfate and exposure of the resulting imine to azidoacetyl chloride-triethylamine in dichloromethane (−78°→0°) affords azetidinone (4).

Oxidative elimination of the phenylselenenyl group (4 to 5) is accomplished by exposure to m-CPBA in dichloromethane at −20° followed by diisopropylamine (−20°→−25°).

Reduction of the azide function in 5 with H₂S-triethylamine in dichloromethane followed by acylation of the resulting amine with the acylating agent of choice affords 7.

Oxidative hydrolysis (7 to 8) of the enamide function is effected by exposure of 7 to p-nitroperoxybenzoic acid in 10:10:1 THF-water-formic acid at 25°.

Initial efforts to prepare 9 from 8 by a diazo-transfer reaction were unsuccessful, probably due to the low kinetic acidity of the target methylene protons and the exceptional acid lability of the diazo function conferred by the p-alkoxyl group. After considerable experimentation, we found that replacement of the acidic amide protons with trimethylsilyl groups (BSTFA-TMSCl-DMAP-CH₃CN) followed by exposure to p-nitrobenzenesulfonyl azide and LiOC(C₂H₅)₃ in THF at −50° afforded diazo compound 9 in low yield. Treatment of 9 with rhodium acetate in toluene at 80° for 30 minutes afforded the cyclonocardicin derivative (10). Hydrogenolysis of the R° protecting groups (Pd(OH)₂, 1 eq. 0.1 N KHCO₃, 1 atm H₂, THF-water-ethanol) affords I as the potassium salt.

The N-acylation reaction 6 to 7 may be accomplished by any of a variety of well known procedures (the analogous reactions in the 6-amido penicillin and 7-amido cephalosporin series are well known and are apposite here) such as treating 6 in a solvent such as methylene chloride, chloroform or the like with an acid chloride calculated to provide the acyl radical R¹ in the presence of from 1–5 equivalents of K₂HPO₄ in water or in the presence of pyridine at a temperature of from 0°–25° C. for from 5 –60 minutes. Preferred acylating agents for this purpose are representatively given below:

φCH₂COCl
φOCH₂COCl

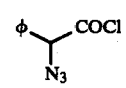

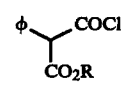

Identification of the Acyl Radical R¹ of Structure I

In the generic representation of the compounds of the present invention (I, above), the acyl radical represented by R¹ can, inter alia, be substituted or unsubstituted: aliphatic, aromatic or heterocyclic, aralphatic or heterocyclylaliphatic carboxylic acid radical, a substituted or unsubstituted: carbamyl radical or a carbothioic acid radical. One group of acyl radicals can be represented by the general formula:

$$-\overset{\overset{X}{\|}}{C}-R''$$

wherein X is O or S and R" represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O, N and S; such above-listed groups can be unsubstituted or can be substituted by radicals such as OH, SH, SR° (R° is lower alkyl or aryl such as phenyl), alkyl or alkoxy groups having 1 to about 6 carbon atoms, halo such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, $\beta,\beta$-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, 1-phenylphenyl, p-aminoethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl benzamidinomethyl and cyclohexylamidinomethyl.

The acyl group can also be a radical of the formula:

wherein X is O or S and n is 0–4, Z represents oxygen, sulfur, carbonyl or nitrogen and R" is defined as above. Representative members of the substituent

that might be mentioned are allylthiomethyl, phenylthiomethyl, butylmercaptomethyl, α-chlorocrotylmercaptomethyl, phenoxymethyl, pehnoxyethyl, phenoxybutyl, phenoxybenzyl, diphenoxymethyl, dimethylmethoxymethyl, dimethylbutoxymethyl, dimethylphenoxymethyl, 4-tuanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)-phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

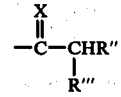

wherein R" is defined as above and R'" is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent:

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(−)-α-hydroxybenzyl, α-carboxybenzyl, α-amino(3-thienyl)-methyl D-(−)-α-amino-3-chloro-4-hydroxybenzyl, α-amino(cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(−)-2-thienyl-guanidinomethyl, D-(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxy-methyl, 3-(1,2-thiazolyl)aminomethyl, 3-(1,2-thiazolyl)-hydroxymethyl, 3-(1,2-thiazolyl)-carboxymethyl, 2-(1,4-thiazolyl- )aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

$$-\overset{O}{\underset{\|}{C}}CHR^3R^4$$

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, aminoethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and jphenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)-acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, aphosphonophenylacetyl, α-amino cyclohexadienylacetyl, α-sulfaminophenylacetyl, α-hydroxyphenylacetyl, α-tetrazolylphenylacetyl and α-sulfophenylacetyl.

Acyls ($R^1$, Structure I) of the following definition are also preferred:

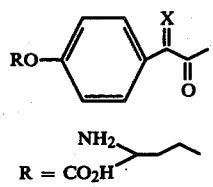

$R = CO_2H$ $X=O, NOR^9$; $R^9=H$, alkyl having 1–6 carbon atoms.

$R^1$ of Structure I may also be a readily removable protecting group; a particularly preferred acyl for this purpose is o or p-nitrobenzyloxycarbonyl.

As noted above, the compounds of the present invention may also generally be represented by the following structural formula:

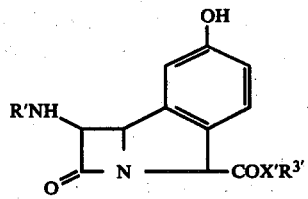

wherein $X'$ is oxygen, sulfur or $NR'$ ($R'$ is hydrogen or loweralkyl having from 1 to 6 carbon atoms); and $R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art; $R^{3'}$ may also be a readily removable blocking group.

Identification of the Radical —COX'R3'

In the generic representation of the compounds of the present invention (I, above the radical represented by —$COX'R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof.

Suitable, but representative, blocking esters $R^{3'}$ (X=0) include those selected from the following list which is representative:

(i) $R^{3'}=CR^aR^bR^c$ wherein at least one of $R^a$, $R^b$, and $R^c$ is an electrondonor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^{3'}=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: $R_3^4SiX'$ wherein $X'$ is a halogen such as chloro or bromo and $R^4$ is alkyl, having 1–6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R3' group at the 3-position; wherein $X'$ is oxygen, sulfur or $NR'$ ($R'$ is H or $R^{3'}$), and $R^{3'}$ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkylportion has 1–6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R$^{3'}$ radicals of the present invention are those wherein (relative to Structure I above), X' is oxygen and R$^{3'}$ is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various Gram-positive and Gram-negative bacteria and accordingly find utility in human and veterinary medicine. Representative pathogens which are sensitive to antibiotics I include: *Straphylococcus aureus, Escherichia coli, Klebsiella pneumoniae, Bacillus subtilis, Salmonella typhosa*, Psuedomonas and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient amy be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined cyclonocardicin antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

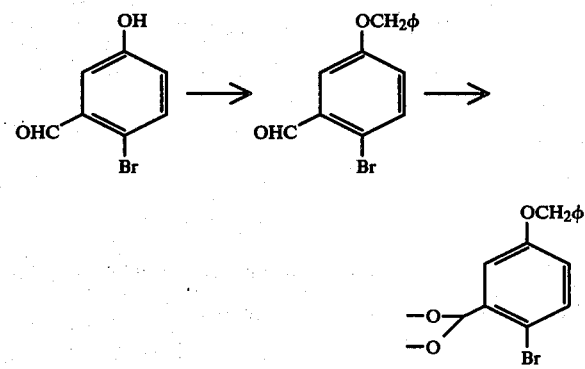

To mixture of 2-bromo-5-hydroxybenzaldehyde (119 g. 0.591 mole) and potassium carbonate (85 g, 0.616 mole) in 1 l. dry acetonitrile is added benzyl bromide (70 ml, 0.59 mole), 0.5 ml triethylamine and 100 mg 18-crown-6 and the suspension is allowed to reflux with stirring for 6 hours. The acetonitrile is removed in vacuo and the resulting thick suspension partioned between 300 ml of water and 500 ml dichloromethane. The aqueous phase is extracted with 200 ml dichloromethane and the combined organics washed with 100 ml 2 M aqueous potassium carbonate, 100 ml water and 250 ml brine, dried over sodium sulfate and filtered through 500 ml silica gel with 1.0 L dichloromethane. The combined eluates are concentrated to 500 ml, treated with Norit, filtered and evaporated to yield 167.2 g pale brown oil. This crude product was dissolved in 1.0 L dry methanol, trimethylorthoformate (88 ml, 0.8 mole) and p-toluene sulfonic acid (1.0 g) is added and the mixture which is stirred at room temperature for 2 hours. Sodium carbonate (5 g) is added, the mixture stirred 2 hours and then concentrated to a thick syrup. The crude product is partioned between 500 ml ether and 100 ml water and the ether layer washed with 100 ml water and 100 ml brine dried over sodium sulfate and evaporated to yield a brown oil. The oil is dissolved in 500 ml hot hexane, decolorized with charcoal and evaporated in vacuo to yield 189 g ether-acetal.

EXAMPLE 2

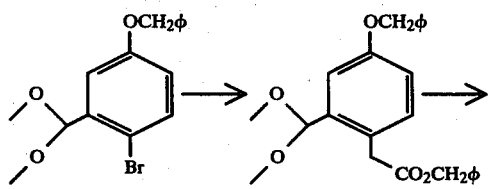

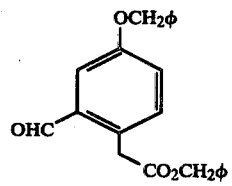

The aryl bromide (67.5 g, 0.20 mole) is dissolved in 800 ml dry THF and the solution cooled to −78°. n-Butyllithium (2.4 M, 83 ml, 0.20 mole) is added dropwise over 15 min. and the solution stirred at −78° 1 hour. The aryl lithium solution is then transferred by 12 ga. cannula to a suspension of copper (I) bromide-dimethylsulfide complex (53 g, 0.258 mole) in 150 ml THF and 6 ml dimethylsulfide at −78° and stirred at that temperature for 2 hours. Benzyl bromoacetate (72 g, 0.315 mole) is then added and the mixture allowed to warm to −10° over 3 hours. Workup with 3.0 L dichloromethane and 3.0 L, pH 9 ammonium chloride buffer yields 119 g. crude product. Purification is effected by chromatography on a waters prep 500 LC with ethylacetate-hexanes as eluant to yield 50.1 g acetal. The acetal is dissolved in 600 ml THF, 500 ml water and 500 ml acetic acid and kept at 30° for 14 hours. Upon concentration to one-half volume the aldehyde (4) separates as white needles, 43 g.

EXAMPLE 3

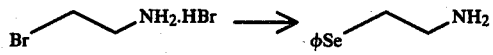

Diphenyl diselenide (25 g, 0.08 mole) is suspended in 400 ml absolute ethanol under nitrogen and sodium borohydride (3.04 g, 0.08 mole) added in portions over 30 min. A solution of 2-bromoethylamine hydrobromide (32.8 g, 160 mole) in 150 ml ethanol is added and the mixture refluxed for 4 hours. The resulting suspension is evaporated to a thick sludge and partioned between 300 ml 2.5 N HCl and 200 ml ether. The aqueous phase is washed with 2×50 ml ether and then brought to pH 11 with 50% aqueous sodium hydroxide. The amine is extracted with 2×200 ml ether and the organic phase is washed with brine, dried over sodium sulfate and evaporated to yield crude amine which is purified by distillation (bp 110° at 0.5 mm).

EXAMPLE 4

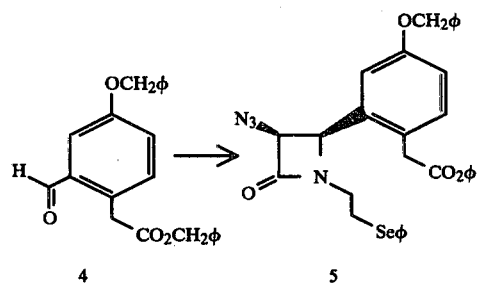

A mixture of aldehyde (4) (3.26 g, 8.9 mmoles), 2-(phenylselenenyl)-ethylamine (1.80 g, 9.0 mmoles) and magnesium sulfate (5.0 g) in 75 ml and chloromethane is stirred at room temperature for 14 hours. The magnesium sulfate is removed by centrifugation and the supernatant is evaporated to yield crude imine. The imine is dissolved in 50 ml dichloromethane and cooled to −78°. Triethylamine (2.24 ml, 16 mmoles) is added followed by dropwise addition of azidoacetyl chloride (1.35 ml, 15 mmoles) in 3.0 ml dichloromethane. The resulting solution is allowed to warm to 0° over 2 hours then worked up with potassium bicarbonate solution to yield 5.48 g crude azetidinone. Chromatography on silica gel with ethylacetate-dichloromethane as eluant affords 5.15 g pure 5 as a yellow glass.

EXAMPLE 5

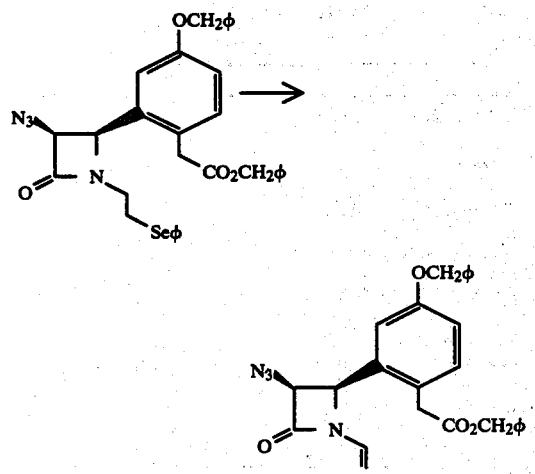

Selenide 5 (4.48 g 7.17 mmoles) is dissolved in 75 ml dichloromethane and cooled to −20°. m-Chloroperbenzoic acid (2.05 g, 10.0 mmoles) is added and the solution is stirred 20 min. Workup with 5 ml aq. sodium sulfite and 50 ml aq. potassium bicarbonate yield a solution which is dried over sodium sulfate and allowed to stand with 2.0 ml diisopropylamine at 30° for 14 hours. The volatiles are then evaporated and the residue chromatographed on silica gel with ethylacetate/dichloromethane as eluant to yield 3.33 g vinyl azetidinone 6.

EXAMPLE 6

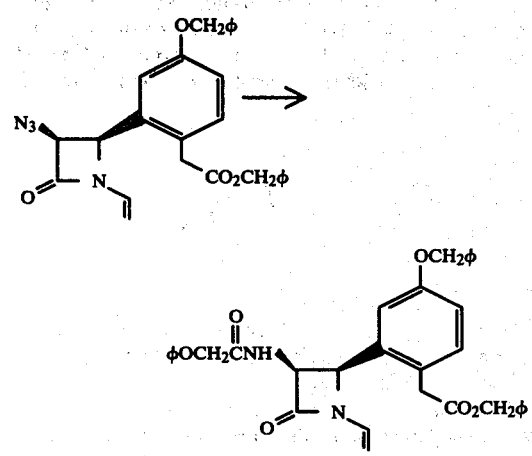

The azide 6 (1.25 g, 2.67 mmoles) is dissolved in 25 ml dichloromethane and 2.0 ml triethylamine and hydrogen sulfide bubbled through the solution for 20 min. The volatiles are removed in vacuo and the residue dissolved in 20 ml dichloromethane and cooled to 0°. Triethylamine (430 ml) and phenoxyacetyl chloride (427 μl) are added and the solution stirred at 0° for 2 hours. Workup with aq. potassium bicarbonate followed by chromatography on silica gel yields 1.28 g pure amide 7.

EXAMPLE 7

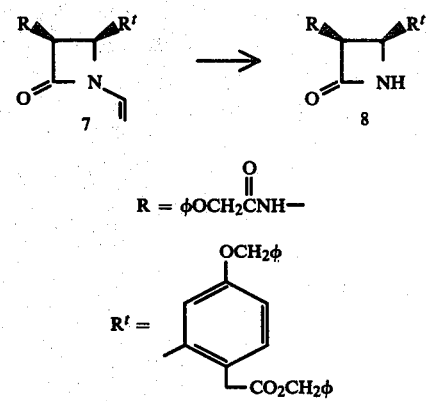

Vinyl azetidinone (530 mg) is dissolved in 5.0 ml THF and 1.0 ml water and p-nitroperoxybenzoic acid (250 mg) is added. After 5 min. 2.0 ml 10% aqueous formic acid is added and the mixture is stirred at 25° 16 hours. The solution is concentrated to remove THF then partioned between dichloromethane and aq. potassium carbonate. The organic phase is evaporated and the crude product purified by chromatography on silica gel with ethylacetate-dichloromethane as eluant to yield 400 mg pure 8.

EXAMPLE 8

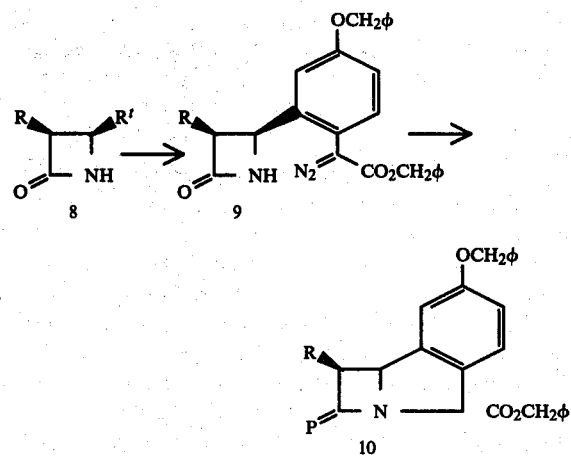

Amide 8 (320 mg) is suspended in 1.0 ml acetonitrile and 1.0 ml bis(trimethylsilyl)trifluoroacetamide is added. After 30 min. 80 μl of trimethyl-silyl chloride is added and the solution stirred 18 hours at 30°. The mixture is co-evaporated three times with dry toluene and pumped at 0.1 mm 18 hours to yield crude disilyl compound. A portion of this material (240 mg) is combined with o-nitrobenzene sulfonyl azide (160 mg) in 5.0 ml dry THF and cooled to −50°. Lithium triethylcarboxide (1.52 M, 265 μl) is added dropwise over 2 min. and the solution allowed to warm to 0° over 2 hours. The solution is cooled to −78°, diluted with 5 ml toluene and worked up at 0° with pH 7 buffer. The organic phase is washed with brine, dried over potassium carbonate at 0° and evaporated 0° in high vacuum. The crude diazo compound is purified by chromatography on Florisl to yield 9, ir 2080 cm$^{-1}$. The diazoester 9 (75 mg) is dissolved in 5 ml dry toluene and 1 mg rhodium (II) acetate added. The mixture is degassed with argon and heated to 80° for 1 hour. Evaporation of solvent and high-speed, low-temperature chromatography on silica gel affords pure 10.

EXAMPLE 9

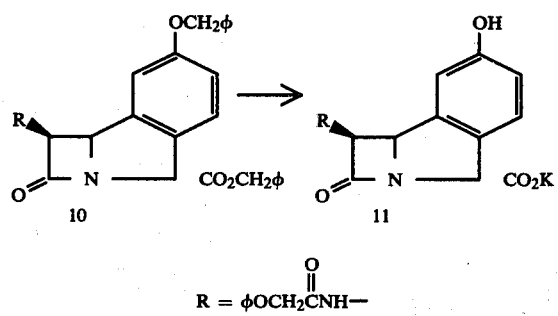

Cyclonocardicin ester 10 (11 mg) is dissolved in 1.0 ml THF and cooled to 0°. A mixture of 0.2 ml EtOH, 0.2 ml water and 0.2 ml 0.1 m potassium bicarbonate was added, followed by 10 mg 20% palladium hydroxide. The mixture is stirred under 1 atm. of hydrogen at 0° for 2 hours, then centrifuged and concentrated to ½ volume at 0°. The residual aqueous solution is washed with 5 ml ether, adjusted to pH 3 with citric acid and extracted with 3×2 ml ethylacetate. The combined ethyl acetate extracts are back-extracted with 5 ml water containing 200 μl of 0.1 potassium bicarbonate and the aqueous solution lyophilized at 0° to yield 11.

EXAMPLE 10

Preparation of Pharmaceutical Compositions

One such unit dosage form is prepared by mixing 120 mg of compound A (the compounds of Example 9) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound of the formula:

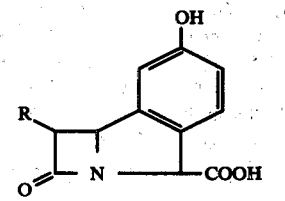

and the pharmaceutically acceptable salts and esters thereof, wherein R is NHR$^1$, R$^1$ is hydrogen, or acyl.

2. A compound according to claim 1 wherein the acyl is selected from the group consisting of phenoxyacetyl, phenylacetyl and

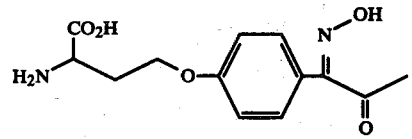

3. An antibiotic method of treatment comprising administering a therapeutically effective amount of a compound according to claim 1.

4. An antibiotic pharmaceutical composition comprising a therapeutically effective amount of a compound according to claim 1 and a carrier therefor.

* * * * *